United States Patent [19]

DuPart et al.

[11] 4,446,119
[45] May 1, 1984

[54] METHOD AND COMPOSITIONS FOR REDUCING CORROSION IN THE REMOVAL OF ACIDIC GASES FROM GASEOUS MIXTURES

[75] Inventors: Michael S. DuPart, Alvin; Billy D. Oakes, Lake Jackson, both of Tex.; David C. Cringle, Melbourne, Australia

[73] Assignee: The Dow Chemical Company, Midland, Mich.

[21] Appl. No.: 372,869

[22] Filed: Apr. 29, 1982

Related U.S. Application Data

[63] Continuation-in-part of Ser. No. 224,365, Jan. 12, 1981, abandoned.

[51] Int. Cl.³ .................. B01D 53/34; C23F 11/06
[52] U.S. Cl. .................................. 423/228; 423/226; 423/229; 252/189; 252/389 R
[58] Field of Search ............. 423/226, 228, 229, 232, 423/233; 252/189, 390, 389.53, 389.54; 422/13

[56] References Cited

U.S. PATENT DOCUMENTS

| | | | |
|---|---|---|---|
| 3,087,778 | 4/1963 | Negro et al. | 423/223 |
| 3,808,140 | 4/1974 | Mago | 252/389 R |
| 3,896,044 | 7/1975 | Mago et al. | 423/229 X |
| 3,959,170 | 5/1976 | Mago et al. | 252/189 |
| 4,071,470 | 1/1978 | Davidson et al. | 423/229 X |
| 4,096,085 | 6/1978 | Holoman, Jr. et al. | 252/189 |
| 4,100,099 | 7/1978 | Asperger et al. | 252/189 |
| 4,100,100 | 7/1978 | Clouse et al. | 252/189 |
| 4,102,804 | 7/1978 | Clouse et al. | 252/189 |
| 4,116,629 | 9/1978 | Ganey et al. | 422/13 |
| 4,143,119 | 3/1979 | Asperger et al. | 423/229 X |

*Primary Examiner*—Earl C. Thomas
*Attorney, Agent, or Firm*—B. G. Colley

[57] ABSTRACT

A corrosion inhibited composition containing a gas conditioning solution such as an alkanol amine with water or with organic solvents and with small amounts of soluble thiocyanate compounds, soluble trivalent bismuth compounds with or without soluble divalent nickel or cobalt compounds. The compositions are useful to separate acid gases such as carbon dioxide from hydrocarbon feed streams in gas conditioning apparatus with minimum amounts of corrosion of the ferrous surfaces.

17 Claims, No Drawings

METHOD AND COMPOSITIONS FOR REDUCING CORROSION IN THE REMOVAL OF ACIDIC GASES FROM GASEOUS MIXTURES

CROSS REFERENCE TO RELATED APPLICATIONS

This application is a continuation-in-part of Ser. No. 224,365 filed Jan. 12, 1981 now abandoned.

BACKGROUND OF THE INVENTION

This invention relates to corrosion inhibiting compositions for use in acid gas removal equipment and methods for their use.

It is well known from the prior art that acid gases such as carbon dioxide, hydrogen sulfide and carbonyl sulfide can be removed from gaseous hydrocarbon feed streams such as natural gas and synthesis gas using dilute aqueous solutions of potassium carbonate, alkanolamines such as monoethanolamine, diethanolamine, and methyl diethanolamine, and other weak bases. The usual procedure is to use a contactor wherein the absorbent solution contacts the feed stream and to use a regenerator with a reboiler wherein the rich absorbent containing the acid gas components is regenerated back to the free absorbent. The solution is then recycled back to the contactor for reuse.

There has been much activity devoted to solving the problem of metallic corrosion in the equipment used in the above process. This problem is particularly acute and/or chronic when mild steel alloys are used in the equipment to save on capital costs over the use of more exotic and expensive metal alloys such as stainless steel. It is, of course, common practice to use stainless steel and nickel alloys in sensitive areas such as heat exchange equipment, regenerator trays and absorber trays.

U.S. Pat. No. 3,087,778 (Apr. 30, 1963) provides for inhibition of potassium carbonate solutions by using 1,000 to 5,000 p.p.m of the trivalent oxides of arsenic, antimony or bismuth.

U.S. Pat. No. 3,808,140 (Apr. 30, 1974) provides for inhibition of alkanolamine solutions by using minor amounts of vanadium and antimony compounds.

U.S. Pat. No. 3,896,044 (July 22, 1975) provides for inhibition of alkanolamine solutions by using minor amounts of nitro substituted aromatic acids or salts thereof.

U.S. Pat. No. 3,959,170 (May 25, 1976) provides for inhibition of alkanolamine solutions using a minor amount of a stannous salt.

U.S. Pat. No. 4,071,470 (Jan. 31, 1978) provides for inhibition of alkanolamine solutions using a minor amount of the reaction product of copper, sulfur, and an alkanolamine.

U.S. Pat. No. 4,096,085 (June 20, 1978) provides for inhibition of alkanolamine solutions using minor amounts of a polyamine, with or without copper, and sulfur.

U.S. Pat. No. 4,100,099 (July 11, 1978) provides for inhibition of sour gas conditioning fluids using minor amounts of quaternary pyridinium salts and alkylene polyamines.

U.S. Pat. No. 4,100,100 (July 11, 1978) provides for inhibition of sour gas conditioning fluids using minor amounts of quaternary pyridinium salts, thiocyanate compounds or thioamide compounds, and divalent cobalt compounds.

U.S. Pat. No. 4,102,804 (July 25, 1978)provides for inhibition of sour gas conditioning solutions using minor amounts of a quaternary pyridinium salt, and a thiocyanate compound, a sulfide compound or a thioamide compound.

U.S. Pat. No. 4,116,629 (Sept. 26, 1978) provides for the corrosion inhibition of stainless steels (types 410 and 430) when in contact with carbonate solutions by using nickel salts.

U.S. Pat. 4,143,119 (Mar. 6, 1979) provides for inhibition of sour gas conditioning solutions using minor amounts of copper and a polysulfide generated in situ.

While the above compositions are effective, they each have various defects which detract from their universal use. For example, compounds of arsenic, antimony and vanadium are known to be toxic and their use presents waste disposal problems for the plant operators. The use of the quaternary pyridinium compounds are known to cause a foaming problem in certain instances.

SUMMARY OF THE INVENTION

It now has been discovered that the corrosion of iron and steel in gas removal equipment containing nickel or nickel alloys can be effectively reduced by using a gas conditioning solution inhibited by effective amounts of a soluble thiocyanate compound in combination with an effective amount of a soluble bismuth compound in the trivalent state.

In the event the acid gas removal equipment contains no nickel or nickel alloys, the gas conditioning solution is further modified by the inclusion of effective amounts of soluble nickel or cobalt compounds in the divalent state.

The inhibitors are constantly replenished or maintained in the gas conditioning solution in order to obtain effective passivation.

The combination of inhibitors claimed herein are unique in that they reduce corrosion of all ferrous surfaces, i.e., not only mild steel but also stainless steel surfaces.

DETAILED DESCRIPTION OF THE INVENTION

The inhibitors of this invention are particularly effective in aqueous solutions of alkanolamines. They are also useful in other weakly basic non-aqueous gas conditioning solutions such as a combination of an alkanolamine and an organic solvent therefore.

Useful alkanolamines which can be used herein are for example; ethanolamine, diethanolamine, triethanolamine, isopropanolamine, diisopropanolamine, N-methyldiethanolamine, 3-dimethylamino-1,2-propanediol, 2-(2-aminoethoxy)ethanol, and mixtures thereof.

These alkanolamines are used in aqueous and organic solutions in amounts of at least 10 percent by weight of the alkanolamine and preferably in the range from 10–50 percent by weight.

Examples of organic solvents that can be used with the above alkanolamines are N-methylpyrrolidone, tetrahydrothiophene dioxide (sulfolane), dioxane, piperazine, 1,4-dimethylpiperazinone and mixtures thereof.

The impure gaseous hydrocarbons feed streams which can be treated with the inhibited gas conditioning solutions of this invention to remove carbon dioxide can contain trace amounts, i.e., 300 parts per million or less of hydrogen sulfide and/or carbonyl sulfide.

Examples of useful soluble thiocyanate compounds are sodium thiocyanate, potassium thiocyanate, and ammonium thiocyanate.

Examples of useful soluble trivalent bismuth compounds are bismuth nitrate, bismuth citrate, bismuth ammonium citrate, bismuth subcarbonate, bismuth halides such as the fluoride, bromide, and chloride, bismuth hydroxide, bismuth subsalicylate, bismuth sulfate, bismuth acetate, bismuth benzoate, bismuth molybdate, bismuth tartrate, bismuth trioxide, and bismuth oxyhalides such as the fluoride, bromide, and chloride.

Examples of useful soluble divalent nickel compounds are nickelous sulfate, nitrate, acetate, tartrate, citrate, and sulfide.

Examples of useful soluble divalent cobalt salts are cobaltous halides such as the chloride, fluoride, and bromide, cobaltous sulfate, cobaltous nitrate, cobaltous acetate, and cobaltous benzoate.

It is to be noted that the terms soluble compound means for the purpose of this invention that the compound is sufficiently soluble in the gas conditioning solution, i.e., aqueous alkanolamine to be useful therein.

It has been found that the inhibitors must be maintained in the gas conditioning solutions in amounts from 50 and preferably 200 or more parts per million of thiocyanate compounds. Since this compound is depleted during use, large amounts such as 500 or more p.p.m. can be used at start-up and periodic additions can be made thereafter to maintain the required effective amounts in the solution.

In the same manner, the effective amount of the trivalent bismuth compounds can range from 1 to 100 p.p.m. and preferably 10 to 25 p.p.m. The effective amount of divalent nickel or cobalt compounds can range from 1 to 100 p.p.m. and preferably 25 to 50 p.p.m.

In the event, the gas conditioning equipment contains stainless steel parts therein, it has been found that a sufficient nickel concentration is obtained in the alkanolamines so that additional nickel salts are not added to obtain the desired corrosion inhibition.

Testing Procedure

The effectiveness of the corrosion inhibitors of this invention were determined in a static coupon corrosion test. In this test a solution of 30 percent by weight of monoethanol amine and 70 percent deionized water was saturated with $CO_2$ to obtain a final solution containing 0.45 to 0.55 moles of $CO_2$ per mole of amine. This solution simulates a rich amine solution commonly found in gas conditioning plants.

About 350 ml of this solution with inhibitors is then placed in a 2" by 10" teflon-lined steel cylinder, prepared metal test coupons were inserted, and the cylinder was sealed and bolted shut.

The cylinder and its contents were then heated to 250° F. for 24 hours. The coupons were then removed, cleaned and weighed. The corrosion rate in mils per year (M.P.Y.) is calculated from the following equation $$M.P.Y. = \frac{(1.44/\text{metal density in gms/cm}^3)\ (\text{weight loss in mgs})}{(\text{surface area in dm}^2)\ (\text{time in days})}$$

In the manner set forth above, Table I gives the corrosion rate using mild steel (1020MS) stainless steel (304SS and 316SS) and Monel coupons at 250° F. over a 24-hour period. The inhibitors used in these tests were ammonium thiocyanate, nickel sulfate and bismuth citrate.

TABLE I

| RUNS | INHIBITOR | METAL CORROSION - MPY | | | |
|---|---|---|---|---|---|
| | | 1020MS | 304SS | 316SS | MONEL |
| Control Example | NONE | 46 | 10 | 5 | 2 |
| 1 | 200 ppm $SCN^-$ + 50 ppm $Ni^{+2}$ + 1 ppm $Bi^{+3}$ | 3.55 | 0.40 | 0.86 | 2.29 |
| 2 | 200 ppm $SCN^-$ + 50 ppm $Ni^{+2}$ + 1 ppm $Bi^{+3}$ | 4.24 | 0.34 | 1.26 | 2.12 |
| 3 | 200 ppm $SCN^-$ + 50 ppm $Ni^{+2}$ + 1 ppm $Bi^{+3}$ | 4.13 | 0.40 | 0.63 | 2.23 |
| 4 | 200 ppm $SCN^-$ + 50 ppm $Ni^{+2}$ + 1 ppm $Bi^{+3}$ | 4.55 | 0.86 | N.A. | N.A. |
| 5 | 200 ppm $SCN^-$ + 50 ppm $Ni^{+2}$ + 1 ppm $Bi^{+3}$ | 4.81 | 1.14 | N.A. | N.A. |
| 6 | 200 ppm $SCN^-$ + 50 ppm $Ni^{+2}$ + 1 ppm $Bi^{+3}$ | 5.17 | 0.80 | N.A. | N.A. |
| 7 | 200 ppm $SCN^-$ + 50 ppm $Ni^{+2}$ + 1 ppm $Bi^{+3}$ | 3.50 | 0.51 | N.A. | N.A. |
| 8 | 200 ppm $SCN^-$ + 50 ppm $Ni^{+2}$ + 1 ppm $Bi^{+3}$ | 3.81 | 0.63 | N.A. | N.A. |
| 9 | 200 ppm $SCN^-$ + 50 ppm $Ni^{+2}$ + 1 ppm $Bi^{+3}$ | 4.43 | 0.17 | N.A. | N.A. |
| 10 | 200 ppm $SCN^-$ + 50 ppm $Ni^{+2}$ + 1 ppm $Bi^{+3}$ | 3.92 | N.A. | N.A. | N.A. |
| 11 | 200 ppm $SCN^-$ + 50 ppm $Ni^{+2}$ + 1 ppm $Bi^{+3}$ | 4.91 | N.A. | N.A. | N.A. |
| 12 | 200 ppm $SCN^-$ + 50 ppm $Ni^{+2}$ + 1 ppm $Bi^{+3}$ | 4.65 | N.A. | N.A. | N.A. |
| 13 | 200 ppm $SCN^-$ + 50 ppm $Ni^{+2}$ + 5 ppm $Bi^{+3}$ | 3.50 | 0.21 | N.A. | N.A. |
| 14 | 200 ppm $SCN^-$ + 50 ppm $Ni^{+2}$ + 5 ppm $Bi^{+3}$ | 3.50 | 0.46 | N.A. | N.A. |
| 15 | 200 ppm $SCN^-$ + 50 ppm $Ni^{+2}$ + 5 ppm $Bi^{+3}$ | 3.87 | 0.21 | N.A. | N.A. |
| 16 | 200 ppm $SCN^-$ + 50 ppm $Ni^{+2}$ + 10 ppm $Bi^{+3}$ | 2.93 | 0.40 | N.A. | N.A. |

TABLE I-continued

| RUNS | INHIBITOR | METAL CORROSION - MPY | | | |
|---|---|---|---|---|---|
| | | 1020MS | 304SS | 316SS | MONEL |
| 17 | 200 ppm $SCN^-$ + 50 ppm $Ni^{+2}$ + 10 ppm $Bi^{+3}$ | 4.13 | 0.34 | N.A. | N.A. |
| 18 | 200 ppm $SCN^-$ + 50 ppm $Ni^{+2}$ + 10 ppm $Bi^{+3}$ | 4.13 | 0.34 | N.A. | N.A. |
| 19 | 200 ppm $SCN^-$ + 50 ppm $Ni^{+2}$ + 25 ppm $Bi^{+3}$ | 5.96 | 0.70 | N.A. | N.A. |
| 20 | 200 ppm $SCN^-$ + 50 ppm $Ni^{+2}$ + 25 ppm $Bi^{+3}$ | 8.21 | 0.34 | N.A. | N.A. |
| 21 | 200 ppm $SCN^-$ + 50 ppm $Ni^{+2}$ + 25 ppm $Bi^{+3}$ | 8.79 | 0.51 | N.A. | N.A. |

Table I shows the dramatic decrease in the corrosion rates for mild steel and stainless steel when using the inhibitors of this invention. While the results with monel are not as good, they are still acceptable when one considers that most acid gas removal equipment is made with mild steel with very little, if any, monel metal parts contained therein. Similar results are obtained when the nickel sulfate is replaced with cobalt sulfate.

EXAMPLES 22 and 23

The testing procedure used for Examples 1–21 was repeated using in place of the aqueous alkanolamine solution a 30 weight percent solution of monoethanolamine or diisopropanolamine in N-methyl pyrrolidone or tetrahydro thiophene dioxide (sulfolane). The inhibitors used in these examples were 50 parts per million (ppm) of nickel sulfate, 200 ppm ammonium thiocyanate, and 5 ppm bismuth citrate.

The results are set forth in Table II.

TABLE II

| | Solution | Inhibitor | Corrosion rate with 1020 steel in MPY |
|---|---|---|---|
| Example | | | |
| 22 | 30% MEA 70% NMP | 50 ppm $Ni^{+2}$ 200 ppm $SCN^-$ 5 ppm $Bi^{+3}$ | 5.6 |
| Control 1 | 30% MEA 70% NMP | none | 96 |
| 23 | 30% DIPA 70% TTD | 50 ppm $Ni^{+2}$ 200 ppm $SCN^-$ 5 ppm $Bi^{+3}$ | 18 |
| Control 2 | 30 DIPA 70% TTD | None | 32 |

MEA = monoethanolamine;
NMP = N—methyl pyrrolidone,
TTD = tetrahydrothiophene dioxide;
DIPA = diisopropanolamine.

The results shown in Table II indicate that non-aqueous solvents such as N-methylpyrrolidone and tetrahydro thiophene dioxide are also useful in this invention. Surprisingly, it was found that dimethylsulfoxide was not useful in this invention.

We claim:

1. A corrosion inhibited composition useful to inhibit corrosion in acid gas removal equipment containing nickel or nickel containing alloys using gas conditioning solutions which comprises
   (A) a gas conditioning solution useful for removing acid gases comprising an aqueous or organic solution of alkanolamines, and
   (B) a mixture comprising
      (1) an effective amount of soluble compounds selected from the group consisting of one or more thiocyanate compounds, and mixtures thereof,
      (2) an effective amount of a soluble bismuth compound in the trivalent state.
2. The composition as set forth in claim 1 wherein the amount of said thiocyanate compounds is from 50 or more parts per million, and the amount of said bismuth compounds is in the range from 1 to 100 parts per million.
3. The composition as set forth in claim 1 wherein the organic solvent used in said solution is selected from the group comprising N-methyl pyrrolidone, tetrahydrothiophene dioxide, dioxane, piperazine, 1,4-dimethyl piperazinone, and mixtures thereof.
4. A corrosion inhibited composition comprising
   (A) a gas conditioning solution useful for removing acid gases comprising an aqueous or organic solution of alkanolamines, and
   (B) a mixture comprising
      (1) an effective amount of soluble compounds selected from the group consisting of one or more thiocyante compounds, and mixtures thereof,
      (2) an effective amount of a soluble bismuth compound in the trivalent state, and
      (3) an effective amount of soluble divalent compounds selected from the group consisting of one or more nickel compounds, one or more cobalt compounds, and mixtures thereof.
5. The composition as set forth in claim 4 wherein the amount of said thiocyanate compounds is from 50 or more parts per million, the amount of said bismuth compounds is in the range from 1 to 100 parts per million, and the amount of said nickel or cobalt compounds is in the range from 1 to 100 parts per million.
6. The composition as set forth in claim 4 wherein the organic solvent used in said solution is selected from the group comprising N-methyl pyrrolidone, tetrahydrothiophene dioxide, dioxane, piperazine, 1,4-dimethyl piperazinone, and mixtures thereof.
7. In the method of separating acid gases such as carbon dioxide from a gaseous hydrocarbon feed stream containing said acid gases by contacting said gaseous stream with a gas conditioning solution comprising an aqueous or organic solution of alkanolamines followed by regeneration of said solution the improvement which comprises inhibiting the corrosion of ferrous equipment used therein by maintaining in said solution,
   (A) a corrosion inhibiting amount of soluble compounds selected from the group consisting of thiocyanate compounds, and mixtures thereof,
   (B) a corrosion inhibiting amount of one or more soluble trivalent bismuth compounds, and (C) a corrosion inhibiting amount of soluble divalent compounds selected from the group consisting of one or more nickel compounds, one or more cobalt compounds, and mixtures thereof.

8. The method as set forth in claim 7 wherein the amount of said thiocyanate or compounds is from 50 or more parts per million, the amount of said bismuth compounds is in the range from 1 to 100 parts per million, and the amount of said nickel or cobalt compounds is in the range from 1 to 100 parts per million.

9. The composition as set forth in claim 7 wherein the organic solvent used in said solution is selected from the group comprising N-methyl pyrrolidone, tetrahydrothiophene dioxide, dioxane, piperazine, 1,4-dimethyl piperazinone, and mixtures thereof.

10. A corrosion inhibited composition useful to inhibit corrosion in acid gas removal equipment containing nickel or nickel containing alloys using aqueous alkanolamine solutions which comprises
 (A) an aqueous alkanolamine solution
 (B) a mixture comprising p2 (1) an effective amount of soluble compounds selected from the group consisting of one or more thiocyanate compounds, and mixtures thereof,
  (2) an effective amount of a soluble bismuth compound in the trivalent state.

11. The composition as set forth in claim 10 wherein the amount of said thiocyanate compounds is from 50 or more parts per million, and the amount of said bismuth compounds is in the range from 1 to 100 parts per million.

12. A corrosion inhibited composition comprising
 (A) an aqueous alkanolamine solution useful for removing acid gases, and
 (B) a mixture comprising
  (1) an effective amount of soluble compounds selected from the group consisting of one or more thiocyante compounds, compounds, and mixtures thereof,
  (2) an effective amount of a soluble bismuth compound in the trivalent state, and
  (3) an effective amount of soluble divalent compounds selected from the group consisting of one or more nickel compounds, one or more cobalt compounds, and mixtures thereof.

13. The composition as set forth in claim 12 wherein the amount of said thiocyanate compounds is from 50 or more parts per million, and the amount of said bismuth compounds is in the range from 1 to 100 parts per million, and the amount of said nickel or cobalt compounds is in the range from 1 to 100 parts per million.

14. A method for inhibiting corrosion of ferrous metal surfaces by alkanolamine solutions containing at least 10 percent by weight of alkanolamines and containing dissolved acid gases which comprises maintaining in said solution:
 (A) a corrosion inhibiting amount of soluble compounds selected from the group consisting of thiocyanate compounds, and mixtures thereof,
 (B) a corrosion inhibiting amount of one or more soluble trivalent bismuth compounds, and
 (C) a corrosion inhibiting amount of soluble divalent compounds selected from the group consisting of one or more nickel compounds, one or more cobalt compounds, and mixtures thereof.

15. The method as set forth in claim 14 wherein the amount of said thiocyanate compounds is from 50 or more parts per million, the amount of said bismuth compounds is in the range from 1 to 100 parts per million, and the amount of said nickel or cobalt compounds is in the range from 1 to 100 parts per million.

16. In the method of separating acid gases from a hydrocarbon feed stream containing said acid gases by contacting said gaseous stream with an aqueous alkanolamine solution at elevated pressure followed by regeneration of said solution at a lower pressure, the improvement which comprises inhibiting the corrosion of ferrous equipment used therein by maintaining in said solution,
 (A) a corrosion inhibiting amount of soluble compounds selected from the group consisting of thiocyanate compounds, and mixtures thereof,
 (B) a corrosion inhibiting amount of one or more soluble trivalent bismuth compounds, and
 (C) a corrosion inhibiting amount of soluble divalent compounds selected from the group consisting of one or more nickel compounds, one or more cobalt compounds, and mixtures thereof.

17. The method as set forth in claim 16 wherein the amount of said thiocyanate compounds is from 50 or more parts per million, the amount of said bismuth compounds is in the range from 1 to 100 parts per million, and the amount of said nickel or cobalt compounds is in the range from 1 to 100 parts per million.

* * * * *

UNITED STATES PATENT AND TRADEMARK OFFICE
CERTIFICATE OF CORRECTION

PATENT NO. : 4,446,119

DATED : May 1, 1984

INVENTOR(S) : Michael S. DuPart, Billy D. Oakes, and David C. Cringle

It is certified that error appears in the above—identified patent and that said Letters Patent is hereby corrected as shown below:

Col. 1, line 44; change "3,808140" to --3,808,140--.

Col. 4, Table I; change heading "METAL CORROSION-MPY" to --METAL CORROSION RATE-MPY--.

Col. 5, Table I cont.; change heading "METAL CORROSION-MPY" to --METAL CORROSION RATE-MPY--.

Col. 5, Claim 1; line 67; change "ton" to --tion--.

Col. 6, Claim 4, line 38; change "thiocyante" to --thiocyanate--.

Col. 7, Claim 10, line 21; delete "p2".

Col. 7, Claim 12, line 38; change "thiocyante" to --thiocyanate--.

Signed and Sealed this

Thirtieth Day of October 1984

[SEAL]

Attest:

GERALD J. MOSSINGHOFF

Attesting Officer

Commissioner of Patents and Trademarks